United States Patent [19]

Chapuis et al.

[11] Patent Number: 5,081,312

[45] Date of Patent: Jan. 14, 1992

[54] 2,2,3,6-TETRAMETHYL-CYCLOHEXANE-CARBALDEHYDE

[75] Inventors: Christian Chapuis, Petit-Saconnex; Christian Margot, Bassins; Karl-Heinrich Schulte-Elte, Onex; Hervé Pamingle, Versoix, all of Switzerland

[73] Assignee: Firmenich SA, Geneva, Switzerland

[21] Appl. No.: 657,917

[22] Filed: Feb. 20, 1991

Related U.S. Application Data

[62] Division of Ser. No. 450,148, Dec. 13, 1988, Pat. No. 5,017,711.

[30] Foreign Application Priority Data

Dec. 21, 1988 [CH] Switzerland ................... 4759/88

[51] Int. Cl.$^5$ .................. C07C 47/28; C07C 47/32
[52] U.S. Cl. .................. 568/446; 549/332; 568/443; 568/447
[58] Field of Search .................. 568/446, 443, 447; 549/332

[56] References Cited

U.S. PATENT DOCUMENTS

| | | | |
|---|---|---|---|
| 4,010,213 | 3/1977 | Naegel | 568/447 |
| 4,636,602 | 11/1986 | Schulte-Elte et al. | 568/822 |
| 4,868,340 | 9/1989 | Fehr et al. | 568/447 |

OTHER PUBLICATIONS

Rosenberger et al., 63 Helv. Chim, Acta., p. 1665 (1980).
Schulte-Elte et al., 68 Helv. Chim. Acta., p. 1961 (1985).
Schappi et al., 30 Helv. Chim. Acta. p. 2199 (1947).

*Primary Examiner*—Warren B. Lone
*Attorney, Agent, or Firm*—Pennie & Edmonds

[57] ABSTRACT

New 4,4,5,8-tetramethyl-1-oxaspiro[2,5]octane. A process for its preparation starting from 2,2,3,6-tetramethyl-1-cyclohexanone is described.

4,4,5,8-Tetramethyl-1-oxaspiro[2,5]octane is a useful raw material for the preparation of 2,2,3,6-tetramethyl-cyclohexane-carbaldehyde, a key intermediate for the synthesis of valuable fragrance ingredients.

1 Claim, No Drawings

2,2,3,6-TETRAMETHYL-CYCLOHEXANE-CARBALDEHYDE

This is a division of application Ser. No. 07/450,148, filed Dec. 13, 1988, now U.S. Pat. No. 5,017,711.

BRIEF DESCRIPTION OF THE DISCLOSURE

The present invention reverts to new 4,4,5,8-tetramethyl-1-oxaspiro[2.5]octane.

This invention provides the said compound in one of its diastereomeric form depicted by formulae

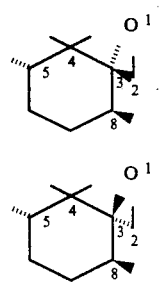

This invention provides further a process for th preparation of 4,4,5,8-tetramethyl-1-oxaspiro[2.5]octane, which process comprises the methylenation of 2,2,3,6-tetramethyl-1-cyclohexanone and the subsequent epoxidation of the obtained 1,2,2,4-tetramethyl-3-methylenecyclohexane.

A further object of the present invention is a process for the preparation of 4,4,5,8-tetramethyl-1-oxaspiro[2.5]octane, which comprises treating 2,2,3,6-tetramethyl-1-cyclohexanone with dimethylsulfonium methylide under the conditions of the Corey-Chaykovsky reaction.

A still further object of the invention is the utilization of 4,4,5,8-tetramethyl-1-oxaspiro[2.5]octane as raw material for the preparation of 2,2,3,6-tetramethyl-cyclohexane-carbaldehyde in a process which consists in treating the said spiro derivative with a Lewis type acid.

This invention provides also 2,2,3,6-tetramethyl-cyclohexane-carbaldehyde under the form of one of the diastereomers of formulae

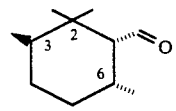

and

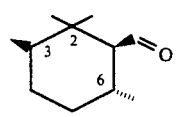

BACKGROUND OF THE INVENTION

European Patent no. 121,828 published on Nov. 19, 1987 (priorities: 4/12/83 and 8/30/83) discloses certain hydroxy compounds of formula

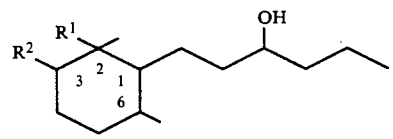

wherein each of symbols $R^1$ and $R^2$ represents a methyl radical or wherein $R^1$ stands for an ethyl radical and $R^2$ represents a methyl radical or a hydrogen atom.

One of the objects of the cited patent is the utilization as fragrance ingredients of the said hydroxy compounds, especially in their trans configuration or in the form of mixtures containing proportions higher than 50% by weight of the trans isomer together with minor amounts of the corresponding cis derivative.

Amongst the compounds defined by generic formula (I), 1-(2,2,3,6-tetramethyl-1-cyclohexyl)-3-hexanol presents a particular interest due to its ambery and animal odorous note which is both elegant and powerful.

The prior art discloses two processes for its preparation [see above cited patent]. One uses 2,3,6-trimethyl-cyclohex-5-en-1-one as starting material according to the following reaction scheme:

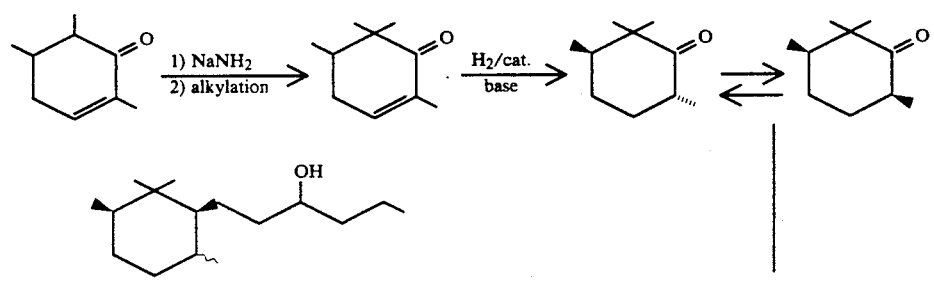

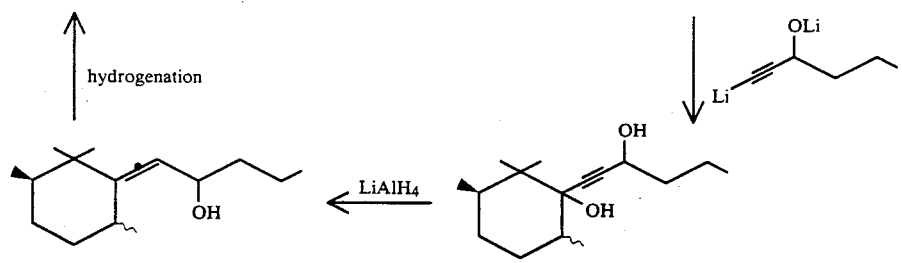

The second process uses certain ester derivatives of α-cyclogeranic acid and can be illustrated by the following reaction scheme:

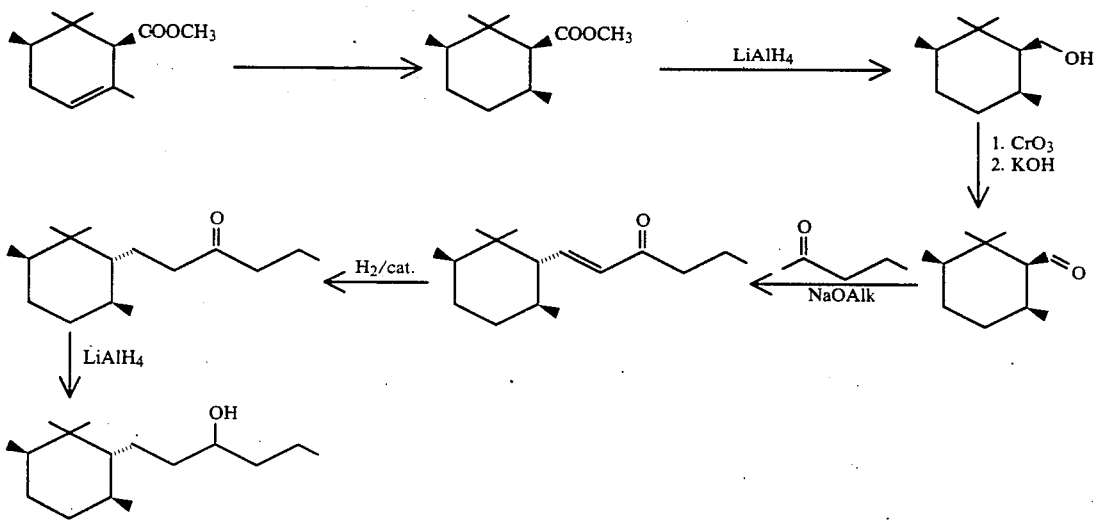

As it becomes apparent from the above given schemes, one of the critical intermediates in this process is 2,2,3,6-tetramethyl-cyclohexane-carbaldehyde.

This invention offers a novel and technically satisfactory solution to the problem of preparing the said aldehyde, namely the compound defined by the following formula

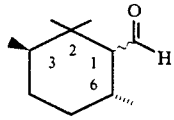

(II)

wherein the wavy line defines a C—C bond of cis or trans configuration, and wherein the two methyl substituents in position 3 and 6 possess the trans configuration.

PREFERRED EMBODIMENTS OF THE INVENTION

The present invention provides a process for the preparation of 4,4,5,8-tetramethyl-1-oxaspiro[2.5]octane which compound can then be converted into useful 2,2,3,6-tetramethyl-cyclohexane-carbaldehyde by treating it with a Lewis type acid. The aldehyde thus obtained possesses a high degree of isomeric purity (equal or higher than 90%). The process of the invention consists in the methylenation of 2,2,3,6-tetramethyl-1-cyclohexanone to give 1,2,2,4-tetramethyl-3-methylene-cyclohexane followed by the epoxidation of the obtained compound to give 4,4,5,8-tetramethyl-1-oxaspiro[2.5]octane.

The following reaction scheme illustrates this process and the conversion of the obtained oxaspiro derivative into 2,2,3,6-tetramethyl-cyclohexane-carbaldehyde:

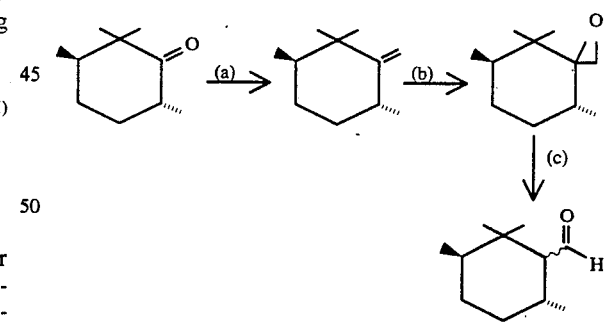

The first step of the process is effected by olefination by Wittig type reaction of tetramethyl-cyclohexanone and triphenyl-methylene-phosphorane in a basic medium. This step is carried out in a manner analogous to that described by L. Fitjer and U. Quadbeck [Synth. Comm. 15, 855 (1985)].

Step (b), which consists in the epoxidation of the methylenic double bond, can be effected according to the usual methods by means of an organic peracid. Suitable peracids include peracetic, trifluoroperacetic, perbenzoic, mono-chloropenbenzoic or perphthalic acid in a chlorinated solvent such as for example chloroform, methylene chloride, trichloroethylene or dichloroethane. Peracetic acid in methylene chloride or dichloroethane is preferred. Buffer agents such as alkali salts of organic acids can be added to the reaction mixture. To this end, it is possible to use sodium or potassium formate, acetate, propionate, butyrate, oxalate, citrate or tartrate. Sodium acetate is preferred.

The obtained epoxide, or 4,4,5,8-tetramethyl-1-oxaspiro[2.5]octane, is a novel chemical entity. Thanks to the above described process, it is now possible to obtain this compound in a well defined stereoisomeric form wherein the two methyl substituents in positions 3 and 6 have the trans configuration one with respect to other as depicted by the following formula

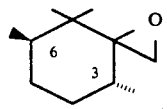  (III)

This enables the preparation of useful 1-(2,2,c-3,t-6-tetramethyl-1-cyclohexyl)-3-hexanol of formula

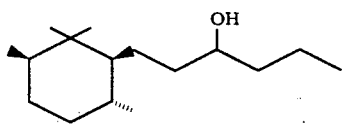  (Ia)

the preferred isomer of advantageous fragrance character. According to another process of the present invention, 4,4,5,8-tetramethyl-1-oxaspiro[2.5]octane is prepared by reacting 2,2,3,6-tetramethyl-cyclohexanone with dimethylsulfonium methylide. The reaction is carried out in accordance with the technic described by E. J. Corey and M. Chaykovsky [J. Am. Chem. Soc. 87, 1353 (1965)] for analogous conversions. Dimethylsulfonium methylide can be prepared in situ by the reaction of sodium hydride, dimethylsulfide and dimethylsulfate in solution in dimethylsulfoxide. The reaction occurs at room temperature or at a temperature in the vicinity of the room temperature. The desired product is then obtained by the usual treatments of separation after washing with water, extraction and fractional distillation. The details of the process shall be described in the examples.

2,2,3,6-Tetramethyl-1-cyclohexanone in their trans isomeric form, used as starting material in the above described process, can be prepared according to the method described by G. Schappi and C. F. Seidel [Helv. Chim. Acta 30, 2199 (1947)]. The present invention relates also to a variant of the above described process. According to this variant, epoxide (III) is obtained by reacting 2,2,3,6-tetramethyl-1-cyclohexanone with dimethylsulfonium methylide, this latter compound is however prepared by the reaction of trimethylsulfonium chloride with sodium hydroxide in dimethylsulfoxide. The here applied reaction conditions are surprising. In fact, M. Rosemberg et al. [Helv. Chim. Acta 63, 1665 (1980)] did describe that the conversion of 2,2,6-trimethyl-cyclohex-5-en-1-one to the corresponding oxirane according to the method suggested by Corey et Chaykovsky [see reference cited above] could be carried out by means of aqueous NaOH in the presence of triethylbenzylammonium chloride under phase transfer reaction conditions. By so doing, the cited authors did observe that such a conversion required specially long reaction time (10 days). Under the reaction conditions defined in the process of the invention, we could observe surprisingly that the conversion into the desired oxirane was complete in about six hours. On the contrary, longer reaction times, of the order of about 18 to 40 hours, were necessary to prepare dimethylsulfonium methylide in situ by reaction of dimethylsulfide and dimethylsulfate with sodium hydroxide in dimethylsulfoxide. One of the objects of the present invention consists precisely in the preparation of 4,4,5,8-tetramethyl-1-oxaspiro[2.5]octane by a process which comprises reacting 2,2,3,6-tetramethyl-1-cyclohexanone and dimethylsulfonium methylide wherein said dimethylsulfonium methylide is formed in situ in the reaction medium by the reaction of a. trimethylsulfonium chloride with sodium hydroxide in dimethylsulfoxide, or b. a mixture of dimethylsulfide and dimethylsulfate with sodium hydroxide in dimethylsulfoxide. The reaction is carried out at a temperature of about 10° to 50° C., preferably at a temperature in the vicinity of room temperature.

According to a preferred embodiment of the invention, NaOH is added to a mixture consisting of 2,2,3,6-tetramethyl-1-cyclohexanone and trimethylsulfonium chloride in dimethylsulfoxide. The reaction is slightly exothermic, hence the necessity to maintain an external cooling of the reaction mixture so as to keep the temperature at about 25°-30° C. Good stirring is also applied for about 6 hr. 4,4,5,8-Tetramethyl-1-oxaspiro[2.5]octane is then obtained by extraction of the resulting mixture with petrol ether, concentration of the organic extracts and fractional distillation As mentioned above, the obtained oxirane can be converted to 2,2,3,6-tetramethyl-cyclohexane carbaldehyde by reacting it with a Lewis acid such as trifluoroboroetherate, titanium tetrachloride or tin tetrachloride. The reaction can also be promoted by other reagents, e.g. metal halides such as $ZnI_2$, $MgBr_2$ or $MgI_2$. The conversion to the desired aldehyde can also be effected by subjecting the oxirane to pyrolysis at a temperature of between about 400° and 500° C.

According to the process of the invention and by using 2,2,3,6-tetramethyl-1-cyclohexanone in the form of a trans/cis (82:18) isomeric mixture, there is obtained 4,4,5,8-tetramethyl-1-oxaspiro[2.5]octane as an isomeric mixture wherein the trans content is predominant, of the order of 95%. The obtained product is especially adapted as a starting material for the preparation of 1-(2,2,3,6-tetramethyl-1-cyclohexyl)-3-hexanol of superior odor quality.

Owing to the presence of an oxiranic ring in its molecule, 4,4,5,8-tetramethyl-1-oxaspiro[2.5]octane can also occur under the form of the stereoisomers defined by the following formulae

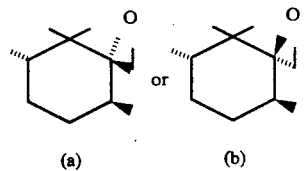

(a)    (b)

The respective content of one or the other of the said isomers can vary slightly as a function of the conditions applied to carry out the reaction. This, however, has no influence on the conversion of 4,4,5,8-tetramethyl-1-oxaspiro[2.5]octane to 1-(2,2,3,6-tetramethyl-1-cyclohexyl)-3-hexanol.

The two diastereoisomers in their pure state can be further obtained starting from optically pure 2,2,t-3,r-6-tetramethyl-1-cyclohexanone according to a process analogous to that described above. Thus starting from (+)-(3S,6S)-2,2,3,6-tetramethyl-1-cyclohexanone with $[\alpha]^{20}_D = +52.2°$, there is obtained (+)-(3S,5S,8S)-4,4,5,8-tetramethyl-1-oxaspiro[2.5]octane with $[\alpha]^{20}_D = +36.0°$.

Starting from (−)-(3R,6R)-2,2,3,6-tetramethyl-1-cyclohexanone with $[\alpha]^{20}_D = -50.7°$, there is obtained (−)-(3R,5R,8R)-4,4,5,8-tetramethyl-1-oxaspiro[2.5]octane with $[\alpha]^{20}_D = -35.1°$.

Although the aldehyde of formula

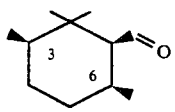

has been disclosed in European patent no. 121,828 and in Helv. Chim. Acta 68, 1961 (1985), its corresponding isomer of formula (II) wherein the two methyl groups in positions 3 and 6 possess the trans cyclanic configuration, is a new compound. It constitutes also one of the objects of this invention.

It can occur in the form of two diastereomers of formula

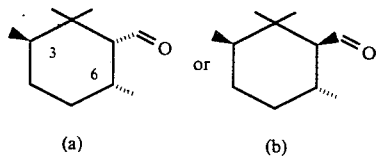

(a)          (b)

The invention is illustrated in a more detailed manner by the following examples without being limited thereto. The temperatures are indicated in degrees centigrade and the abbreviations have the meaning usual in the art.

EXAMPLE 1

Preparation of 4,4,t-5,r-8-tetramethyl-1-oxaspiro[2.5]octane a. 43 g (0.38M) of potassium tert-butoxide and 155 g (0.38M) of triphenylmethylphosphonium iodide in 600 ml of anhydrous toluene were introduced in a three neck round bottom vessel equipped with a thermometer, a condenser and a dropping funnel. The mixture was kept under a nitrogen atmosphere and refluxed for 1.5 h. The condenser was then replaced by a distillation head and toluene was distilled off, whereupon 45 g (0.29M) of 2,2,t-3,r-6-tetramethyl-1-cyclohexanone were added thereto. The reaction mixture was kept at 130° for 1.5 h, cooled and poured on crushed ice and finally extracted with ether. The combined organic extracts were washed with an aqueous saturated solution of NaCl until neutrality, dried over Na₂SO₄, filtered and concentrated. On distillation, the obtained residue gave 33 g of a colorless oil having b.p. 48°/3 mmHg consisting of 2,2,t-3,r-6-tetramethyl-1-methylene-cyclohexane. The product was identical in all respects to a sample prepared according to the method described by G. Schäppi et al. [Helv. Chim. Acta 30, 2199 (1947)].

b. 29 g (0.19M) of the compound obtained as indicated under letter a. above, 7.8 g (0.095M) of sodium acetate and 60 ml of methylene chloride were introduced in a three neck vessel equipped with a condenser, a thermometer and a dropping funnel. The reaction mixture was cooled at 0° and 50 g (0.3M) of peracetic acid at 40% in acetic acid were added dropwise. The reaction is slightly exothermic. After having been stirred at room temperature for 1 h, the obtained mixture was poured on a saturated aqueous solution of NaCl while the organic phase was separated. After washing until neutrality, the organic phase was dried over Na₂SO₄, filtered and concentrated, whereupon the residue was distilled to give 27.6 g of a colorless oil having b.p. 64°/3.5 mmHg; yield: 86%. The analytical characters of the obtained product were the following:

¹H-NMR (360 MHz): 0.695(3H,d,J=3 Hz); 0.75(3H,s); 0.85(3H,d,J=7 Hz); 0.93 and 0.945(3H,2s); 2.59–2.75(2H,m)δppm;

MS: M⁺ = 168(11); m/z: 153(66), 139(13), 123(91), 111(31), 107(11), 96(48), 81(100), 67(41), 55(68), 41(63).

EXAMPLE 2

Preparation of 4,4,t-5,r-8-tetramethyl-1-oxaspiro[2.5]octane 16.1 ml (168.8 mM) of dimethyl sulfate were introduced in a three neck vessel equipped with a mechanical stirrer and a dropping funnel and 12.4 ml (170 mM) of dimethylsulfide were added thereto under an argon atmosphere. The reaction mixture was cooled to 0° as soon as its temperature showed a tendency to increase, then 20 ml of dimethylsulfoxide were added thereto with the consequence that the formed salt went in solution. After having withdrawn the cooling bath, the mixture was stirred during 10 min and cooled again to 20°.

At this temperature, 5.4 g (168.8 mM) of sodium hydride at 75% in mineral oil were added and the mixture was stirred for 30 min, then cooled to 0°. 20 g (129.9 mM) of 2,2,t-3,r-6-tetramethyl-1-cyclohexanone were added dropwise and the resulting mixture was stirred at 20° for 15 h.

100 ml of ethyl acetate were added, followed by slow addition of 400 ml of water. The aqueous layer once separated was extracted successively with 100 ml of petrol ether (30°–50°), 100 ml of ethyl acetate and again with 100 ml of petrol ether (30°–50°). The combined organic phases were washed with 2 fractions of 100 ml each of a saturated aqueous solution of NaCl, then with water. After drying over Na₂SO₄, filtration and evaporation, 23.6 g of a colorless oil was obtained which upon distillation in a bulb-to-bulb apparatus gave 20.5 g of the desired product (yield 89%).

EXAMPLE 3

Preparation of 4,4,t-5,r-8-tetramethyl-1-oxaspiro[2.5]octane 14.57 g (71.43 mM) of trimethylsulfonium iodide and 2.3 g (71.43 mM) of sodium hydride at 75% in mineral oil were introduced in an apparatus as described in above Example 2. The mixture was cooled to 20° and 30 ml of dimethylsulfoxide were added thereto, followed after 30 min by 10 g (64.94 mM) of 2,2,t-3,r-6-tetramethyl-1-cyclohexanone in solution in 10 ml of dimethylsulfoxide. After having been left at room temperature for 24 h, the mixture was treated as indicated in the previous example to give 9.9 g of the desired oxirane with a purity of 97% (yield 88%).

EXAMPLE 4

Preparation of 4,4,t-5,r-8-tetramethyl-1-oxaspiro[2.5]octane

A. Starting from trimethylsulfonium chloride 150 g (1.33M) of trimethylsulfonium chloride and 156 g (0.95M; purity 94%) of 2,2,t-3,r-6-tetramethyl-1-cyclohexanone in 500 ml of anhydrous dimethylsulfoxide were introduced in a 1 l flask equipped with a condenser and a stirrer. 240 g (6M) of NaOH pellets were added to the reaction mixture under vigorous stirring. After 15 min, the temperature of the mixture did raise to 30° and this temperature was kept constant by applying an external cooling. The course of the reaction was followed by GC monitoring. The reaction was completed in 6 h 15 min.

The mixture was then diluted with 200 ml of petrol ether and the resulting mixture was poured onto a mixture of ice/water. The organic phases were separated and added to a fraction of 100 ml of the petrol ether prior used to wash the organic phase. Their concentration gave a residue which, by fractional distillation on a 20 cm column filled with helices, yielded a fraction of 158 g with b.p. 41°–43°/0.8 mmHg of the desired oxirane of 95% purity (yield 94%).

B. Starting from a mixture of dimethylsulfide and dimethylsulfate

A mixture of 1.3 l of dimethylsulfoxide, 185 g (3M) of dimethylsulfide and 340 g (2.7M) of dimethylsulfate was introduced in a 2 l reaction vessel. This mixture was kept under mild stirring while its temperature raised slowly up to 50°. The temperature was kept at this value with an external cooling. When the temperature decreased spontaneously, the external cooling was removed and the temperature was allowed to settle to room temperature. Sodium hydroxide pellets were then added [660 g (16.5M)] to the mixture, followed by 350 g (2.3M) of 2,2,t-3,r-6-tetramethyl-1-cyclohexanone and the obtained mixture was kept under stirring for 18–40 h. The follow-up was carried out as described in the previous example and 355 g of the desired oxirane of 92% purity were obtained (yield 87%).

EXAMPLE 5

Preparation of 2,2,c-3,t-6-tetramethyl-r-1-cyclohexane-carbaldehyde 10 g (59.5 mM) of the epoxide obtained according to the process described in one of the previous examples (see Examples 1 to 4) in 200 ml of toluene were mixed with 2 ml of trifluoroboroetherate in a nitrogen atmosphere and at room temperature during 15 min. The reaction mixture was then poured onto ice, washed with a saturated aqueous solution of NaCl and the organic phase was separated.

By the usual treatments of drying over $Na_2SO_4$, filtration and concentration at reduced pressure, 10 g of the desired aldehyde were obtained after epimerization with NaOMe/MeOH.

The spectral characters were the following:

IR: 1710 cm$^{-1}$.

$^1$H-NMR (360 MHz): 0.805(3H,d,J=6.4 Hz); 0,83(3H,d,J=6.4 Hz); 0,91(3H,s); 0,96(3H,s); 1,01(1H,ddd,J=4; 12.6; 25.2 Hz); 1.15–1.24(1H,m); 1.36(1H,ddd,J=4; 12.6; 25.2Hz); 1.41–1.5(1H,m); 1.6(1H,dd,J=5.4; 10.8); 1.73–1.82(1H,m); 1.9–2.08(1H,m); 9.67(1H,d,J=5.4 Hz) δ ppm.

MS: 168(M+, 9); m/z: 161(0), 145(0), 139(2), 135(8), 124(21), 109(11), 98(42), 83(100), 69(62), 55(85), 41(44).

EXAMPLE 6

Preparation of (+)-(3S,5S,8S)-4,4,5,8-tetramethyl-1-oxaspiro[2.5]octane and (−)-(3R,5R,8R)-4,4,5,8-tetramethyl-1-oxaspiro[2.5]octane By carrying out the reaction as indicated in Examples 2 to 4 above and using (+)-(3S,6S)-2,2,3,6-tetramethyl-1-cyclohexanone having $[\alpha]^{20}_D = +52.2°$, the desired product was obtained with $[\alpha]^{20}_D = +36.0°$.

By using instead (−)-(3R,6R)-2,2,3,6-tetramethyl-1-cyclohexanone with $[\alpha]^{20}_D = -50.7°$, there was obtained (−)-(3R,5R,8R)-4,4,5,8-tetramethyl-1-oxaspiro[2.5]octane with $[\alpha]^{20}_D = -35.1°$.

The specific rotation was measured on pure samples.

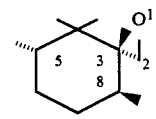

3,8-cis, 5,8-trans $^1$H-NMR (360 MHz): 0.695(3H,d,J=7 Hz); 0.75(3H,s); 0.84(3H,d,J=7 Hz); 0.93(3H,s); 2.65(2H,J=4 Hz) δ ppm.

$^{13}$C-NMR: 15.25(q); 16.42(q); 18.98(q); 20.82(q); 30.04(d); 31.31(t); 32.76(t); 32.76(t); 37.95(s); 38.39(d); 45,84(t); 65.22(s) δ ppm.

MS: M+ = 168; m/z: 153(90), 139(19), 123(91), 111(31), 107(15), 95(42), 81(95), 67(36), 55(68), 41(100).

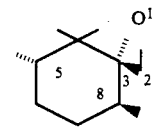

3,8-trans, 5,8-trans $^1$H-NMR (360 MHz): 0.695(3H,d,J=7 Hz); 0.75(3H,s); 0.86(3H,d,J=7 Hz); 0.94(3H,s); 2.62(2H,J=5 Hz) δ ppm.

$^{13}$C-NMR: 15.1(q); 16.0(q); 17.0(q); 22.4(q); 31.0(t); 31.1(d); 34.4(t); 38.1(s); 42.2(d); 45.2(t); 66.1(s) δ ppm.

MS: M+ = 168; m/z: 153(90), 139(19), 123(91), 111(31), 107(15), 95(42), 81(95), 67(36), 55(68), 41(100).

By converting the two epoxides according to the process described in Example 5, the corresponding aldehydes were obtained. Their analytical characters were the following:

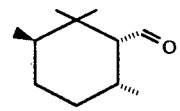

IR: 1710 cm$^{-1}$.

$^1$H-NMR (360 MHz): 0.88(3H,d,J=7 Hz); 0.89(3H,d,J=7 Hz); 0.897(3H,s); 0.945(3H,s); 1.76–1.93(1H,m); 1.93(1H,t,J=6 Hz); 1.93–2.06(1H,m); 10.015(1H,d,J=6 Hz) δ ppm.

MS: M+ = 168; m/z: 153(1), 135(6), 124(6), 109(8), 97(16), 91(4), 84(100), 69(30), 55(48), 41(27).

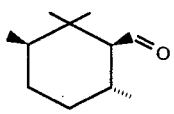

IR: 1710 cm$^{-1}$.

$^1$H-NMR (360 MHz): 0.805(3H,d,J=6.4 Hz); 0.83(3H,d,J=6.4 Hz); 0.91(3H,s); 0.96(3H,s); 1.01(1H,J=4; 12.6; 25.2 Hz); 1.15-1.24(1H,m); 1.36(1H,ddd,J=4; 12.6; 25.2 Hz); 1.41-1.5(1H,m); 1.6(1H,dd,J=5.4; 10.8 Hz); 1.73-1.82(1H,m); 1.9-2.08(1H,m); 9.67(1H,d,J=5.4 Hz) δ ppm.

$^{13}$C-NMR: 15(q); 15.2(q); 20.7(q); 27.7(q); 28.1(d); 30.6(t); 34.7(t); 36.7(s); 41.8(d); 67.6(d); 207.7(d) δ ppm.

MS: M+ = 168; m/z: 161(0), 145(0), 139(2), 135(8), 124(21), 109(11), 98(42), 83(100), 69(62), 55(85), 41(44).

The two enantiomers of 2,2,3,6-tetramethyl-1-cyclohexanone, used as starting materials in the above described process, can be prepared from (−)-(S)-β-citronellol and (+)-(R)-pulegone, respectively. The processes followed are illustrated by the following reaction schemes:

Scheme A

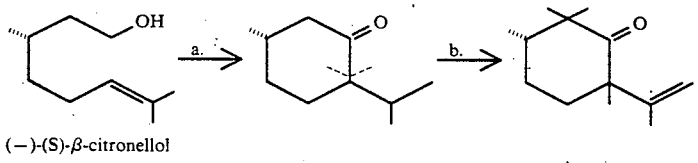

(−)-(S)-β-citronellol

Scheme B

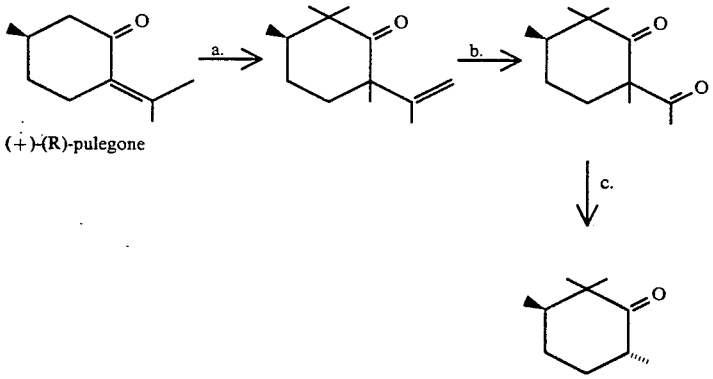

(+)-(R)-pulegone

A. Preparation of (+)-(3S,6S)-2,2,3,6-tetramethyl-1-cyclohexanone a. 10 l of CH$_2$Cl$_2$ and 1704 g (7.89M) of pyridinium chlorochromate were introduced in a four neck reaction vessel equipped with a mechanical stirrer, a thermometer, a condenser and an inlet tube for nitrogen. To this mixture and under nitrogen, 400 g (2.56M) of (−)-(S)-β-citronellol were added while the temperature was kept at 15°-20°. Stirring was then carried on for 60 h at room temperature. After filtration, the mixture was extracted with CH$_2$Cl$_2$ and the combined organic extracts were washed with 15% HCl, saturated NaHCO$_3$, then with water until neutrality. Evaporation and distillation on residue at 7.8 mmHg gave 206.9 g of (−)-pulegone and (−)-isopulegone (40:60) (yield 37%). B.p. 62°/7.8 mmHg).

b. 50 g (1.25M) de KH at 20% in mineral oil were introduced into a flask equipped with a condenser containing 1000 ml of anhydrous tetrahydrofurane, whereupon 51 g (0.34M) of (−)-pulegone were added dropwise thereto. The reaction is slightly exothermic and it was completed by heating to reflux for 2 h. After having lowered the temperature to about 45°, the ordinary condenser was replaced by a CO$_2$/acetone condenser and 78 ml (1.25M) of CH$_3$I were added to the mixture dropwise. Stirring was carried on for one hour at room temperature, then 85 ml of water were precautiously added, whereupon the reaction mixture was poured onto ice. By extraction with ether, washing with water, drying and concentration, 213 g of residue were obtained which on distillation gave 58 g of (+)-(3S)-6-isopropyl-2,2,3,6-tetramethyl-1-cyclohexanone; b.p. 82°/7.8 mmHg.

c. A mixture of 238.7 g of the ketone obtained sub letter b. above at 52% (corresponding to 124.8 g of pure ketone; 0.6M) and 620 ml of ethyl acetate was cooled to −10° while a flow of ozone was passed through the mixture during 6 h until the reaction did not show any sign of exothermicity. 240 ml of dimethylsulfide were introduced dropwise under nitrogen at −10° After having left the temperature to reach room temperature, the mixture was stirred overnight. The mixture was then concentrated, diluted with ether and the organic extracts were subjected to the usual treatments to give 242.1 g of residue. (+)-(3S)-6-acetyl-2,2,3,6-tetramethyl-1-cyclohexanone was obtained at b.p. 76°/6.2 mmHg (yield 44%).

d. 148.8 g of the ketone obtained sub letter c. above (purity 35%; corresponding to 52.08 g of pure ketone; 0.27M) in admixture with 114.7 g (2.05M) of KOH pellets and 4000 ml of ethanol were heated at reflux for 2 h. The mixture was concentrated and then extracted with petrol ether (30°-50°). The combined extracts were subjected to the usual treatments and gave by evaporation 95.6 g of residue. On fractional distillation with a Fischer type column, 27.1 g of the desired ketone were obtained. B.p. 56°/5.8 mmHg.

B. Preparation of (−)-(3R,6R)-2,2,3,6-tetramethyl-1-cyclohexanone 89.1 g (2.23M) of 35% KH in mineral oil were introduced in a reaction vessel containing 2000 ml of anhydrous tetrahydrofurane, whereupon 96.7 g (0.636M) of (+)-pulegone were added dropwise thereto at 15°-20°. The reaction was carried on as indicated sub letter A.b. above by using 139 ml of CH$_3$I (2.23M). 64.3 g (yield 52%) of (−)-(3R)-6-isopropenyl-2,2,3,6-tetramethyl-1-cyclohexanone were thus obtained. The product obtained was then treated in a manner analogous to that indicated sub letters A.c. and A.d. to give (−)-(3R,6R)-2,2,3,6-tetramethyl-1-cyclohexanone.

What we claim is:

1. 2,2,3,6-Tetramethyl-cyclohexane-carbaldehyde in the form of a diastereomer of formula

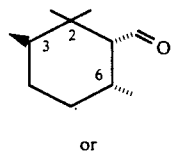

(a)

or

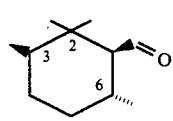

(b)

* * * * *